(12) United States Patent
Axelsson et al.

(10) Patent No.: US 8,911,816 B2
(45) Date of Patent: Dec. 16, 2014

(54) COATING COMPOSITION AND USE THEREOF

(76) Inventors: Johan Claes Wilhelm Axelsson, Stockholm (SE); Fredrik Robin Lechard Lilieblad, Hagersten (SE)

(*) Notice: Subject to any disclaimer, the term of this patent is extended or adjusted under 35 U.S.C. 154(b) by 332 days.

(21) Appl. No.: 13/144,070

(22) PCT Filed: Jan. 20, 2010

(86) PCT No.: PCT/SE2010/000009
§ 371 (c)(1), (2), (4) Date: Jul. 11, 2011

(87) PCT Pub. No.: WO2010/085195
PCT Pub. Date: Jul. 29, 2010

(65) Prior Publication Data
US 2011/0274820 A1    Nov. 10, 2011

(30) Foreign Application Priority Data
Jan. 20, 2009   (SE) ...................... 0950015

(51) Int. Cl.
| | | |
|---|---|---|
| A61K 9/36 | (2006.01) | |
| B05D 1/18 | (2006.01) | |
| A23G 3/24 | (2006.01) | |
| B05C 3/00 | (2006.01) | |
| A61K 9/28 | (2006.01) | |
| A61J 3/00 | (2006.01) | |

(52) U.S. Cl.
CPC ............ *A61K 9/286* (2013.01); *A61K 9/2873* (2013.01); *A61K 9/2893* (2013.01); *A61J 3/005* (2013.01); *A61K 9/282* (2013.01); *A61K 9/2826* (2013.01)
USPC .... 427/2.14; 427/346; 427/434.7; 427/434.4; 118/13; 118/18; 118/26; 118/30; 424/488; 424/480

(58) Field of Classification Search
None
See application file for complete search history.

(56) References Cited

U.S. PATENT DOCUMENTS

| | | | | |
|---|---|---|---|---|
| 3,935,686 | A * | 2/1976 | Dozois | 52/302.7 |
| 4,176,175 | A * | 11/1979 | Maekawa et al. | 424/480 |
| 5,676,990 | A * | 10/1997 | Wawrzynski | 426/305 |
| 6,517,887 | B1 * | 2/2003 | Lilieblad | 427/2.14 |
| 2004/0013732 | A1 * | 1/2004 | Farber et al. | 424/488 |

* cited by examiner

*Primary Examiner* — Cachet Sellman
(74) *Attorney, Agent, or Firm* — Kipa AB; Tomas Friend

(57) ABSTRACT

The present invention relates to a new coating composition and especially a new coating composition to be used with a specific coating device for providing an even, thin and enclosing coating on tablets, capsules or pills of different sizes and shapes in order to improve the taste and the swallowing characteristics of the tablets, capsules or pills.

18 Claims, 7 Drawing Sheets

Figure 6a
Figure 6b
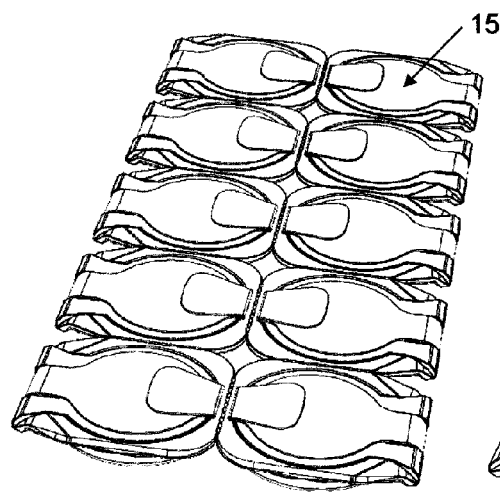
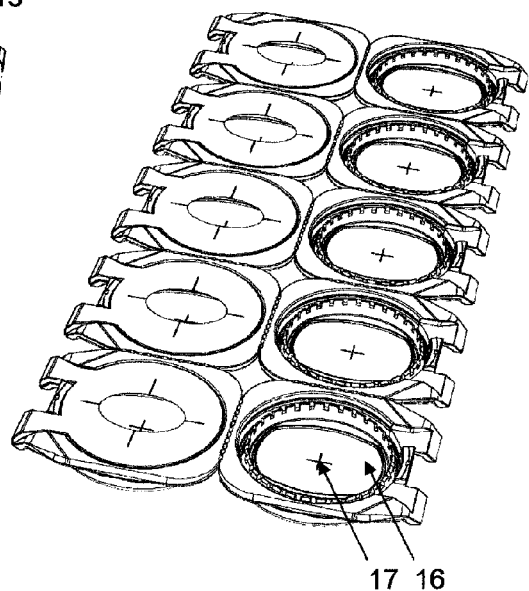
Figure 6c
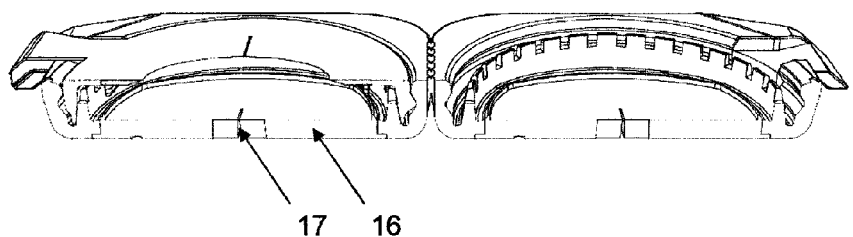

COATING COMPOSITION AND USE THEREOF

BACKGROUND OF THE INVENTION

EP-B1-1 176 950 relates to a method and a disposable device for providing a coating on a tablet, capsule, pill or the like, in order to improve the taste and the swallowing characteristics of the tablet. The coating is applied manually with the device and it replaces the taste of a given tablet with a more palatable taste. EP-B1-1 176 950 is incorporated in a whole as a reference.

Many types of substances can be used with this coating technique in order to apply a coating to a tablet. The present inventors have however discovered that in order to be able to coat different types of tablets, in size and shape, with the same device (which is advantageous since it is less economical and practical to produce different devices adjusted for different sizes and shapes of tablets) and still obtain an enclosing coating that is thin and even you need to have a coating composition presenting specific viscoelastic rheological properties at room temperature. The reason why it is beneficial with a fully enclosing coating is that it better can camouflage a tablet's possible bitter taste and also better improve the swallowability of tablets with a rough surface. The reason why it is beneficial with a thin and even thickness of the coating is that if the coating is uneven the coating could get too thick on some areas making the tablet's size bigger and therefore harder to swallow. If the coating is too thin on some parts the coating could dissolve too quickly in the mouth, revealing the sometimes bad taste and rough surface of a tablet. A coating composition with a suitable viscoelastic rheology can be reshaped and stretched to a great extent forming a thin and even film and is therefore suitable to be used with this coating technique.

The patent EP-B1-1176950 gives little advice in how to formulate a suitable coating composition. The only examples of ingredients suggested to be used in EP-B1-1176950 to formulate the coating composition are gelatine and glucose and no directions are given concerning the amount of the ingredients to be used. When using only gelatine and glucose the present inventors have not succeeded in formulating a stable viscoelastic coating composition that is suitable for coating of different types of tablets, in size and shape with the same device.

The formula with best rheological properties using only gelatine, glucose and water was obtained by dissolving gelatine (type A, 260 bloom, SG-722 from Gelita Sweden) and glucose separately in water and then mix it and boil it and ascertain that the final compound consists of 1.3 weight-% gelatine, 1.0 weight-% water and 97.7 weight-% glucose. However, this composition is not stable and will crystallize within two weeks resulting in that the viscoelastic properties are lost and the composition becomes a non-homogenous mass with hard sugar crystals, not suitable for the coating technique. This formula would therefore at its best result in a product with a shelf life of less than two weeks, which naturally is very disadvantageous for a consumer product.

Further on a coating composition consisting of gelatine, glucose and water gives a coating that is relatively sticky to fingers and teeth. The stickiness to fingers is negative since it makes the coating less pleasant when the coated tablet is held in the hand before swallowing. The stickiness may also increase the amount of dirt and bacteria etc. that clings to the tablet before swallowing. The stickiness to teeth is negative since the coated tablet may therefore cling to the teeth when the tablet is put into the mouth, which is unpleasant and it can also make the swallowing of the coated tablet more difficult. It is therefore desirable to have a coating compound with a relatively low stickiness.

Play putties based on cross linked polymer solution often have a suitable stable visco elastic rheology. Further these play putties are generally non sticky to fingers and teeth. However, these types of masses are not suitable to be used as coating compositions mainly since these compounds contain borax, which is not permitted as a food additive in many countries and since they have a low solubility in water which can delay the absorption of an ingested drug in the stomach. The present inventors have albeit much effort not succeeded in finding a previous developed suitable viscoelastic mass based on food approved ingredients.

Tests were also performed on many different confectionary masses but it was found that none of these had suitable viscoelastic properties. Generally they were either mostly elastic (e.g. jelly confectionary) or mostly viscous (e.g. soft caramel).

Apart from the above mentioned desirable properties of the coating compound the inventors have found that it would also be preferable if the coating composition could be sugar free, contain saliva stimulating ingredients, be slippery in the mouth in order to make the tablet easier to swallow, be allergen free, has a low water activity preventing bacterial growth, be easy to deposit into the device during manufacturing, dissolve quickly from the tablet in the stomach and contain only ingredients not known to interact with medical substances.

It is an object of the present invention to solve the above mentioned obstacles and present a suitable coating composition to be used with the coating method and device described in EP-B1-1176950.

SUMMARY OF THE INVENTION

The foregoing problems are solved by a visco elastic coating composition according to the present invention. Therefore, it is an object of the present invention to provide a new coating composition and especially a coating composition to be used with the coating method and device such as described in EP-B1-1176950 and in the examples below, for providing an even, thin and enclosing coating on tablets, capsules or pills of different sizes and shapes in order to improve the taste and the swallowing characteristics of the tablets, capsules or pills. Sugar free coating compositions of the coating compound is also disclosed.

The invention discloses a coating composition comprising (a) Carbohydrates: 50-93.5 weight-%, (b) Gelatine: 0.1-20 weight-%, (c) Water: 1.0-35 weight-% wherein the carbohydrates constitutes of a mix of different carbohydrates, for use with a device for enclosing application of a coating on a tablet, a capsule, a pill or the like, wherein the device comprises of a bowl formation 4 containing the coating composition 5 and exhibiting a bottom 11 which includes an elastic diaphragm 12, 16 having a centrally located, conveniently penetrable opening 13, 17 permitting passage of the tablet 3 and the simultaneous application thereon of a thin layer of said coating composition 5 for providing a coating on a tablet, a capsule a pill or the like. Preferably the coating composition for enclosing application of a coating on a tablet, a capsule, pill or the like should contain 0.3-15 weight-% gelatine.

The coating composition for enclosing application of a coating on a tablet, a capsule, a pill or the like wherein the coating composition 5 also comprises:

| (d) Fat: | 5-40 weight-% |
| (e) Emulsifier | 0.01-10 weight-%. |

The invention also discloses a coating composition for enclosing application of a coating on a tablet, a capsule, a pill or the like wherein the coating composition 5 has a pH that deviates at least 2 steps, preferably at least 3 steps and more preferably 4 steps from the isoelectric point of the gelatine in the composition.

The invention also discloses a disposable device for enclosing application of a coating on a tablet, a capsule, a pill or the like wherein the coating composition 5 has a pH that deviates at least 2 steps, preferably at least 3 steps and more preferably 4 steps from the isoelectric point of the gelatine in the composition.

The invention also discloses a disposable device for enclosing application of a coating on a tablet, a capsule, a pill or the like wherein the coating composition can also comprise a pH adjusting agent, preferably present in an amount of between 0.01-10 weight-% and more preferably present in an amount of 0.1-5 weight-%.

The invention also discloses a disposable device for enclosing application of a coating on a tablet, a capsule, a pill or the like where the carbohydrates in the coating composition can be selected from the group consisting of monosaccharides, oligosaccharides, polysaccharides, hydrogenated monosaccharides, hydrogenated oligosaccharides or hydrogenated polysaccharides or any combination thereof.

The invention also discloses a disposable device for enclosing application of a coating on a tablet, a capsule, a pill or the like where the carbohydrates in the coating composition can be selected from the group consisting of syrups containing a combination of carbohydrates of different sorts such as starch syrup (e.g. corn syrup), maltose syrup, sorbitol syrup, maltitol syrup, isomalt syrup and polyglycitol syrup.

The invention also discloses a disposable device for enclosing application of a coating on a tablet, a capsule, a pill or the like wherein the coating composition can at 0.1 Hz frequency have an elastic modulus (G') between 10-1000 000 Pa and a viscous modulus (G") of between 10-1000 000 Pa and at 10 Hz an elastic modulus (G') between 100-100 000 000 Pa and a viscous modulus (G") between 100-100 000 000 Pa.

The invention further discloses a coating composition for application of a coating on a tablet, a capsule, a pill or the like comprising:
(a) Carbohydrates: 50-93.5 weight-% (dry substance)
(b) Fat: 5-40 weight-%
(c) Gelatine: 0.3-15 weight-%
(d) Emulsifier: 0.01-10 weight-%
(e) Water: 1.0-35 weight-%
wherein the carbohydrates constitutes of a mix of different carbohydrates.

The coating composition can also have a pH that deviates at least 2 steps, preferably at least 3 steps and more preferably 4 steps from the isoelectric point of the gelatine in the composition.

The coating composition can also comprise a pH adjusting agent, preferably present in an amount of between 0.01-10 weight-% and more preferably present in an amount of 0.1-5 weight-%.

The carbohydrates in the coating composition can also be selected from the group consisting of monosaccharides, oligosaccharides, polysaccharides, hydrogenated monosaccharides, hydrogenated oligosaccharides or hydrogenated polysaccharides or any combination thereof.

The carbohydrates in the coating composition can also be selected from the group consisting of syrups containing a combination of carbohydrates of different sorts such as starch syrup (e.g. corn syrup), maltose syrup, sorbitol syrup, maltitol syrup, isomalt syrup and polyglycitol syrup.

The coating composition can at 0.1 Hz frequency have an elastic modulus (G') between 10-1000 000 Pa and a viscous modulus (G") of between 10-1000 000 Pa and at 10 Hz an elastic modulus (G') between 100-100 000 000 Pa and a viscous modulus (G") between 100-100 000 000 Pa.

It is further disclosed a device for enclosing application of a coating on a tablet, a capsule, a pill or the like, wherein a bowl formation 4 containing a coating composition 5 according to any of the above combinations, and exhibiting a bottom 11 which includes an elastic diaphragm 12, 16 having a centrally located, conveniently penetrable opening 13, 17 permitting passage of the tablet 3 and the simultaneous application thereon of a thin layer of said coating composition 5 for providing a coating on a tablet, a capsule a pill or the like.

It is also disclosed the use of a coating composition according to any of the above mentioned coating compositions and combinations of coating compositions for enclosing application of a coating on a tablet, a capsule, a pill or the like.

The coating composition has a rheology showing strain hardening viscosity during extension. Further on, the coating composition has a water activity of less than 0.8, preferably less than 0.7 and most preferably below 0.6. The coating composition could also comprise a saliva stimulating agent(s), colouring agent(s), a flavouring agent(s) and be sugar free.

A further example of a coating composition comprises:
(a) Maltitol syrup: 60-85.80 weight-% (dry substance)
(b) Fat: 10-30 weight-%
(c) Gelatine: 0.5-5 weight-%
(d) Sugar Ester: 0.2-3 weight-%
(e) Water: 3-12 weight-%
(f) Citric Acid: 0.5-4 weight-%

A further example of a coating composition comprises:
(a) Maltitol syrup: 63-79 weight-% (dry substance)
(b) Fat: 15-25 weight-%
(c) Gelatine: 0.6-3 weight-%
(d) Sugar Ester: 0.2-2 weight-%
(e) Water: 4-8 weight-%
(f) Citric Acid: 0.7-3 weight-%

BRIEF DESCRIPTION OF THE DRAWINGS

FIG. 6*a*) shows an alternative example of a card comprising ten disposable devices for coating tablets, FIG. 6*b*) shows the same ten devices but with the foil removed and in the right row of five devices is also the lid normally partially covering the bowl formations removed and FIG. 6*c*) shows a cross-section of two devices from FIG. 6*b*).

DETAILED DESCRIPTION OF THE INVENTION

Figure 1:
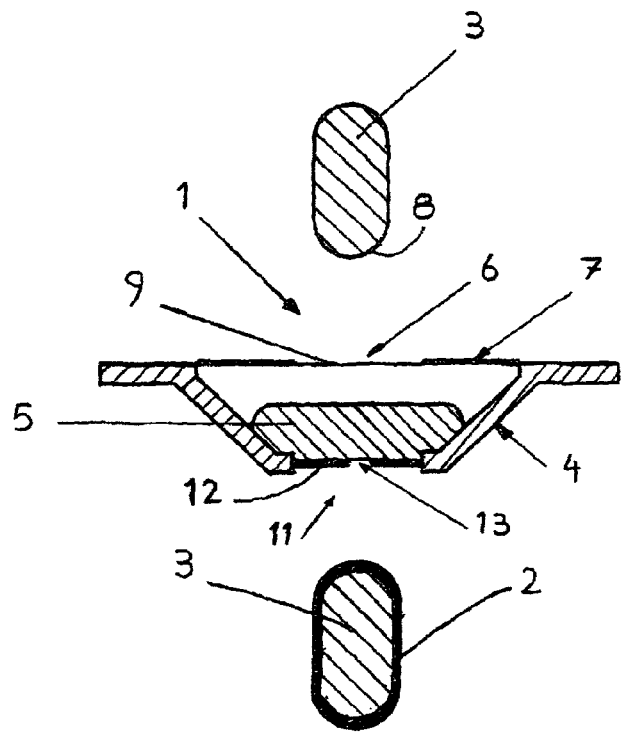
FIG. 1 is a cross-section through a disposable device for the application of a coating in accordance with the invention.
Figure 2:
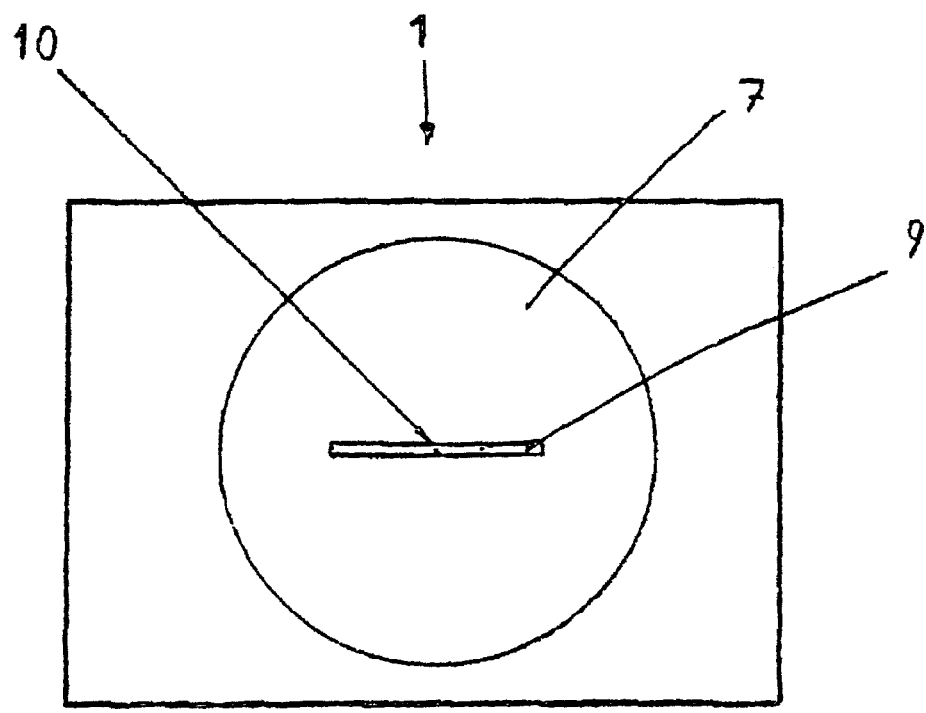
FIG. 2 is a top view of the device shown in FIG. 1.

Different embodiments of a disposable device which can be used according to the present invention will now be described. FIGS. 1-4, shows an example of a disposable device 1 disclosed in detail in EP-B1-1 176 950 adapted to apply a coating 2 on a tablet, a capsule, a pill or the like 3. The device 1 comprises at least one bowl formation 4 housing a coating composition 5 according to the present invention. The top wall or opening 6 of bowl formation 4 is covered by a foil 7, e.g. made of tinfoil or of a plastic material, which is either detachable or can conveniently be penetrated by the front edge portion 8 of tablet 3. In order to facilitate a penetration of foil 7, if it has not been detached, it can be provided with a weakened zone 9 at its central portion 10. The bottom 11 of the bowl formation 4 includes an elastic diaphragm 12 of rubber, plastic or the like, which has a centrally located, easily penetrable opening or weakened zone 13 permitting a tablet 3 to pass and at the same time applying a thin layer of coating composition 5 according to the present invention on tablet 3.

Figure 3:
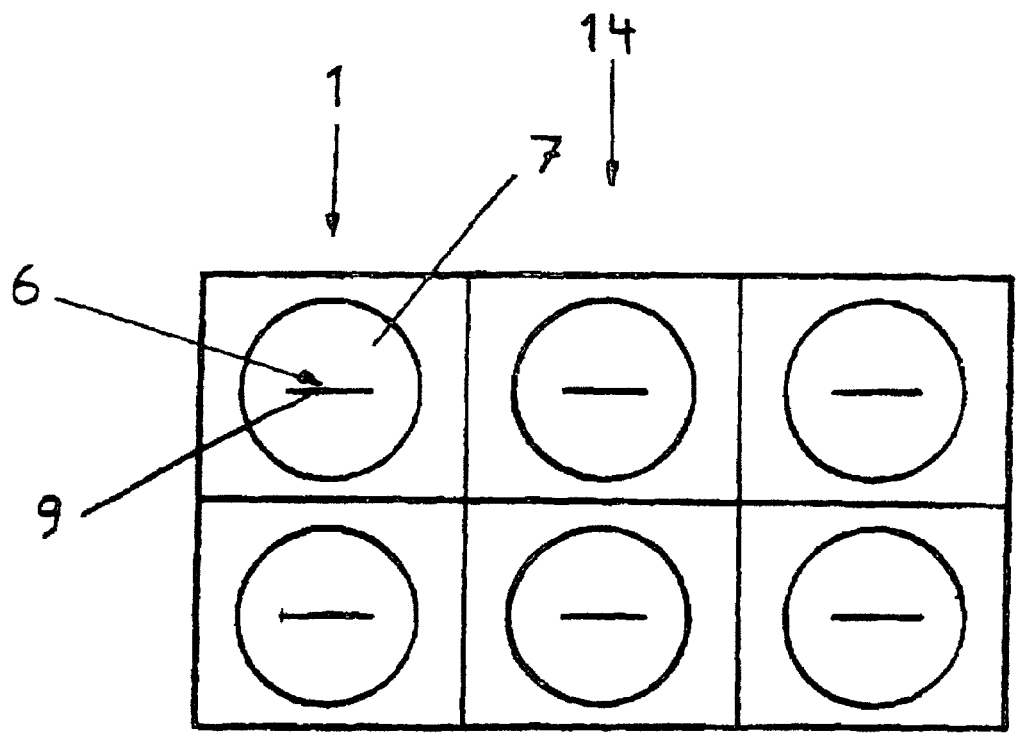
FIG. 3 is a top view of a card comprising six devices according to FIGS. 1 and 2.
Figure 4:
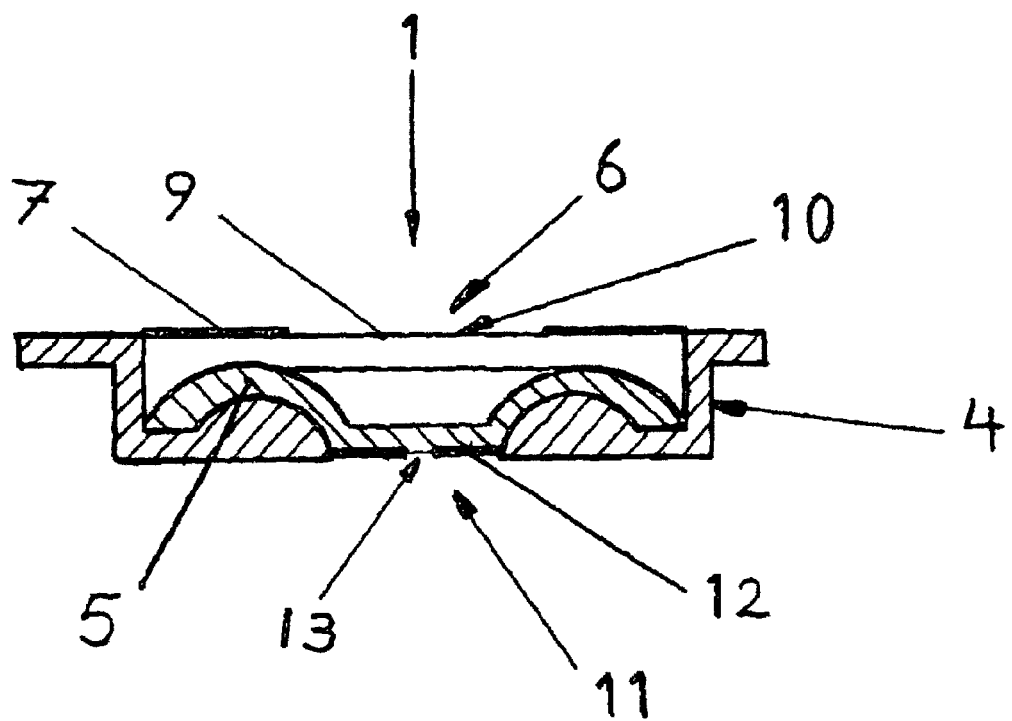
FIG. 4 is a diagrammatic lateral view illustrating an alternative embodiment of a device according to the invention, adapted to apply a coating composition in a pre-formed shape.
Figure 5:
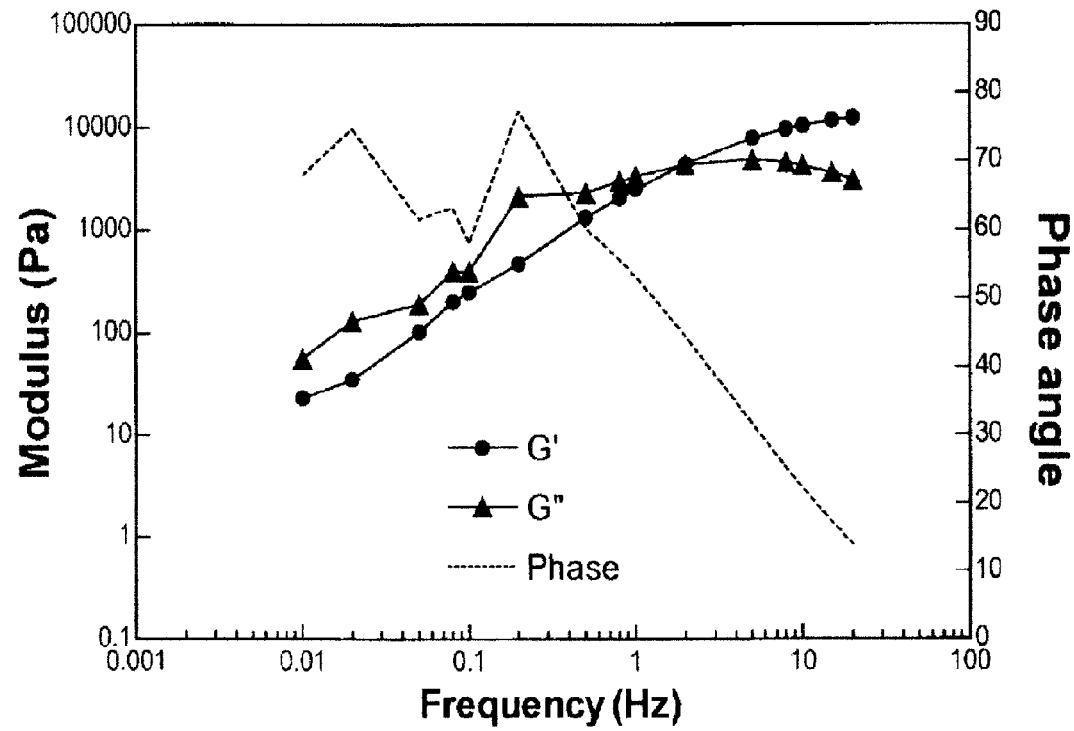
FIG. 5 shows a graph illustration of the rheology of a play putty which was found to have a suitable rheology.
Figure 5:
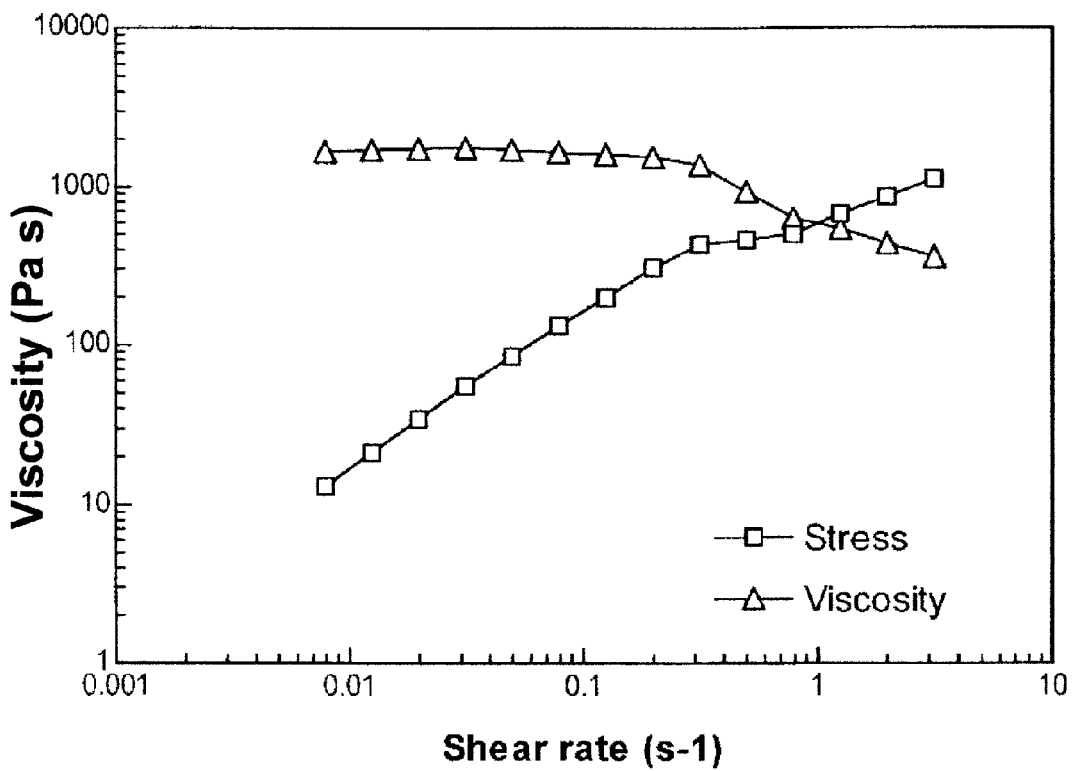

In connection with retail sale to consumers a plurality of bowl formations 4, which contains a coating composition according to the present invention 5, may be disposed adjacent each other and held together by cards 14 as shown in FIG. 3. However, the disposable devices could also be held together as disclosed in FIG. 6a) to 6b). A cross-section view of the embodiment is also disclosed.

When a coating composition 5 is to be applied to a tablet 3 one does either first detach the foil 7 or push the tablet 3 through foil 7 into direct contact with the composition and then out through the openings 13 centrally located in the diaphragm 12. The opening does then get wider and shapes the coating composition 5 to an even coating 2 consisting of a film enclosing all of the tablet. This design makes it possible to apply coatings on tablets of most types and sizes.

Further disclosed in the present application is a method for providing a coating composition 5 according to the present invention on a tablet, a capsule, a pill or the like by means of a disposable device and wherein the coating 2 is applied to enclose the tablet 3 while the latter is pushed through a bowl formation 4 containing a coating composition 5 according to the present invention and exhibiting a bottom 11 with an elastic diaphragm 12 which, during the passage-of the tablet 3, surrounds the tablet and simultaneously applies a film of a coating composition 5 disclosed in the present invention on the tablet when it passes out through a penetrable opening or weakened zone 13 in the centre of the diaphragm 12.

The device shown in FIGS. 6a-c shows another example of an alternative embodiment of the device. The foil 15 covering the opening in the lid and the opening 17 in the membrane 16 is made of a plastic aluminium laminate. The most essential part of the device, the membrane 16, is soft and elastic and made of a SEBS material with a shore A hardness of around 30. The rest of the device is more rigid and it is made of a mix of low density polyethylene and polypropylene. The dimensions of the oval membrane are 16×12×1.20 mm and the membrane opening 17 in the form of a cross is 2.4×2.4 mm. The outer dimensions of a single device are 21.0×23.5×3.5 mm. The inner dimensions of each cavity are 16.5×2 mm and each of the ten cavities holds about 0.58 grams of coating composition. The outer dimensions of the whole card comprising 10 devices as shown in 6a are 104×47.3×3.5 mm. A friction reducer or release agent could also during manufacturing be applied to the inner parts of a device, especially to the membrane 16. The friction reducer could assure that the coating composition can glide more easily on the membrane during the coating procedure and thereby improve the smoothness and evenness of the resulting coating on the tablet. This possible friction reducer could probably be selected from the group consisting of the following food approved ingredients; fat, E422, E1520, E473, E900, E901, E902, E903, E904, E905, E907, E908, E912, E913 or E914.

As mentioned in the background the inventors found that when using a special combination of glucose, gelatine and water the formula with the best rheological properties was spoiled by crystallization shortly after manufacture. The inventors also tested other types of mono and disaccharides such as fructose and sucrose instead of glucose but they also resulted in crystallization of the mass within a few weeks of storage. It was found that the crystallization could be prevented by replacing the glucose with a mix of carbohydrates of different types. The present inventors realized that after the composition has been manufactured (mixed and boiled) the glucose in the mass can start to crystallize during storage if it is super saturated, if the glucose molecules are arranged close to each other in the compound and if the viscosity of the mass is not sufficiently high to maintain the glucose in a glass state. The present inventors found that using the carbohydrate mix corn syrup 40 DE instead of glucose could inhibit crystallization. Corn syrup is a viscous liquid starch hydrolysate of mono, di, and higher saccharides dissolved in water and it is made by enzymatic hydrolysis of starch. It seems that by mixing different sorts of carbohydrate molecules (as in corn syrup) each sort of carbohydrate is less likely to start to crystallize since there are other sorts of carbohydrate molecules between the carbohydrate molecules of the same sort, which inhibits the molecules to join together and form crystals, and related to that each carbohydrate sort is present in relative low amounts compared to only using e.g. glucose making each carbohydrate less saturated. When replacing the glucose with corn syrup 40 DE and increasing the water content to about 12.5 weight-%, but maintaining the 1.3 weight-% gelatine content the composition got a similar rheology as the mass with glucose, but it did not start to crystallize during storage. However, it was found that after a few days storage the gel strength of the mass decreased substantially, which made the mass mainly viscous and therefore quite unsuitable for this coating technique. Also other combinations of corn syrup and gelatine giving a similar viscosity resulted in that the gel strength diminished during storage.

After extensive laboratory work the inventors unexpectedly reached the finding that by changing the pH in the composition, the diminishing of the elasticity could be avoided. Lowering the pH to about 2.5 by adding 2 weight-% citric acid and maintaining the water content at 12.5 weight-% resulted in a stable mass where the elasticity did not change significantly during storage. Repeated experiments showed that also 1 weight-% citric acid gave the same results.

Another advantage of adding citric acid is that the composition becomes saliva stimulating because of the low pH. The saliva stimulating effect is beneficial for this coating invention since it can make it easier to swallow tablets, especially for patients/users with Xerestomi (low saliva flow), which many elder people with swallowing disorders have. Replacing the citric acid with the same amount of malic acid results in the same advantage regarding the stability and the saliva stimulating effect. However, citric acid is preferred by the inventors since it according to them gives the best taste. It was also found that if increasing the pH to a high level and using a type B gelatine a good stability was also achieved. In this case the inventors used the same amount of a 220 bloom type B gelatine (Bovine Hide 220 bloom, PLK142R from Gelita Sweden) and added 3% trisodium citrate to increase the pH to about 7.5 or 0.036% sodium hydroxide to increase the pH to about 8.2. An increased pH however results in a decreased saliva stimulating effect. After numerous laboratory experiments it was discovered that the low stability when using only corn syrup 40 DE and gelatine and not adjusting the pH probably had to do with that the gelatine precipitated because of the low amount of available water in the compound since the longer polysaccharides in the corn syrup absorbs a high proportion of the water in the composition.

By lowering or increasing the pH in the composition, the pH deviates from the isolectric point of the gelatine. The pH at which the charge of gelatine in solution is neutral is known as the isoelectric point. The inventors have preferred to use a type A pig skin gelatine which has an isoelectric point of 7-9, in comparison to type B gelatine that has an isoelectric point of 4.8-5.2. The more the pH of a compound that contains gelatine deviates from the isoelectric point of the gelatine, the more the gelatine molecule charge will be, which improves the performance and solubility of the gelatine, which lowers the risk for precipitation. Because of this unexpected effect, both the pH of the compound and the type of gelatine affects the stability of the coating composition. After experimentation the inventors found that in order to get a stable compound wherein the elasticity is maintained the pH of the coating composition should deviate from the isoelectric point with at least 2 steps, e.g. if the gelatine has an isoelectric point of 5, the composition should have a pH of 3 or lower or a pH of 7 or higher. To achieve this deviation, different gelatine types can be selected and pH modifiers could be used. Preferably the composition's pH should deviate at least 3 steps, and more preferably the composition should deviate at least 4 steps from the isoelectric point of the composition. A general recipe based on this information could comprise:
Carbohydrates of different sorts: 50-98.6 weight-%
Gelatine: 0.3-15 weight-%
pH adjusting agent: 0.01-10 weight-%
Water: 1-35 weight-%

The ingredients should be formulated so that the pH of the composition deviates at least 2 steps, preferably 3 steps and more preferably 4 steps from the isoelectric point of the gelatine, and at 0.1 Hz the elastic modulus (G') should be between 10-1 000 000 Pa and the viscous moldulus (G") between 10-1000000 Pa and at 10 Hz the elastic modulus (G') should be between 100-100 000 000 Pa and the viscous modulus (G") should be between 100-100 000 000 Pa. (Measured with a Stresstech Rheometer, Reologica Instruments, Lund, Sweden. Using a plate-plate geometry with a plate diameter of 30 mm and a gap of 3 mm, in an oscillating mode within the spectrum of 0.001 Hz-10 Hz at 21 degrees Celsius, 50% RH).

An example of a composition could comprise:
Corn syrup 40 DE (dry substance): 76-94 weight-%
Gelatine, type A 260 bloom: 0.5-4 weight-%
Citric acid: 0.5-3 weight-%
Water: 5-17 weight-%

An example of a specific formula could comprise:
Corn syrup 40 DE (dry substance): 84.2 weight-%
Gelatine, type A 260 bloom: 1.3 weight-%
Citric acid: 2 weight-%
Water: 12.5 weight-%

As described in the background the composition should preferably have as low stickiness to teeth and fingers as possible. The present inventors found that by adding fat to the composition so that the fat constituted 18 weight-% of the final composition and lowering the water content to 9.5 weight-% to get a similar viscosity as without the fat the stickiness decreased. However, during storage the fat separated from the mass and migrated out on to the surface, limiting the stability. In order to overcome the separation problem an emulsifier, such as 0.2 weight-% lecithin (E322, e.g. Leciprime 1550 from Cargill) or 0.5 weight-% mono- and diglycerides from fatty acids (E471, e.g. Cremodan 60 VEG from Danisco) was added to the composition. The fat is thereby maintained in the mass and the composition got stable, and the lowered stickiness was maintained. Below is an example of a general recipe also containing fat and emulsifier:
Carbohydrates of different sorts: 50-93.5 weight-% (dry substance)
Fat: 5-40 weight-%
Gelatine: 0.3-15 weight-%
Emulsifier: 0.01-10 weight-%
Water: 1-20 weight-%
pH adjusting agent: 0.01-10 weight-%

Below is an example of a preferred composition containing fat and emulsifier:
Carbohydrates of different sorts: 55-90 weight-% (dry substance)
Fat: 7-35 weight-%
Gelatine: 0.3-9 weight-%
Emulsifier: 0.025-8 weight-%
Water: 1-20 weight-%
pH adjusting agent: 0.01-10 weight-%

Below is an example of a more preferred composition containing fat and emulsifier:
Carbohydrates of different sorts: 60-85.8 weight-% (dry substance)
Fat: 10-30 weight-%
Gelatine: 0.5-5 weight-%
Emulsifier: 0.05-5 weight-%
Water: 1-20 weight-%
pH adjusting agent: 0.01-10 weight-%

The inventors have also found that to use 0.5 weight-% of the emulsifier sugar ester (E473, e.g. Ryoto S-570 from Mitsubishi-Kagaku) as emulsifier further lowers the stickiness to teeth.

As described in the background the coating mass should preferably be sugar free, in order to be gentle on teeth and suitable for diabetics. As source of sugar free carbohydrates of different sorts the inventors found maltitol syrup to be suitable. Maltitol syrup is a hydrogenated high maltose glucose syrup (e.g. Maltidex M 16313 from Cargill). Maltitol syrup was among other reasons selected because of its relative high sweetness. However, the addition of fat and emulsifier and the substitution of the corn syrup to maltitol syrup changed the viscosity of the coating composition. The inventors realized that with these changes the water content must be deceased to get a rheology that is similar to before.

Suitable compositions with maltitol syrup and sugar ester may contain:
Maltitol syrup: 60-85.8 weight-% (dry substance)
Fat: 10-30 weight-%
Gelatine: 0.5-5 weight-%
Sugar Ester: 0.2-3 weight-%
Water: 3-12 weight-%
Citric Acid: 0.5-4 weight-%

Examples of preferable compositions may contain:

| Ingredient | Amount |
|---|---|
| Maltitol syrup E965 (ii) | 63-79 weight-% (dry substance) |
| Vegetable fat | 15-25 weight-% |
| Gelatine (type A) | 0.6-3 weight-% |
| Citric acid E330 | 0.7-3 weight-% |
| Sugar ester E473 | 0.2-2 weight-% |
| Colour | 0.01-2 weight-% |
| Flavour | 0.01-2 weight-% |
| Water | 4-8 weight-% |

The amount of the pH adjusting agent in the recipes above should be selected so that the pH of the mass deviates at least 2 steps, preferably 3 steps and more preferably 4 steps from the isoelectric point of the gelatine. Moreover, the amount of the ingredients in the recipes above should be selected so that at 0.1 Hz the elastic modulus (G') of the coating compound is between 10-1000 000 Pa and the viscous moldulus (G") is between 10-1000 000 Pa and so that at 10 Hz the elastic modulus (G') of the coating compound is between 100-100 000 000 Pa and the viscous modulus (G") is between 100-100 000 000 Pa. (Measured with a Stresstech Rheometer, Reologica Instruments, Lund, Sweden. Using a plate-plate geometry with a plate diameter of 30 mm and a gap of 3 mm, in an oscillating mode within the spectrum of 0.001 Hz-10 Hz at 21 degrees Celsius, 50% RH).

An example of the most suitable composition contains:

| Ingredient | Amount | Brand | Manufacturer |
|---|---|---|---|
| Maltitol syrup E965 (ii) | 68.60 weight-% (DS) | Maltidex M 16313 | Cargill Nordic A/S |
| Vegetable fat | 21.08 weight-% | Cremoflex L plus | Hobum Oele und Fette GmbH |
| Gelatine (type A, 260 bloom) | 1.32 weight-% | SG 722-Low viscosity | Gelita Sweden AB |
| Citric acid E330 | 1.90 weight-% | Citronsyra 1-Hydrat | Univar AB |
| Sugar ester E473 | 0.50 weight-% | Ryoto Sugar Ester S-570 | Mitsubishi Kagaku Food Corp. |
| Colour, e.g. curcumin 10% | 0.30 weight-% | e.g. K12205 | Kanegrade Limited |
| Flavour, e.g. citrus extract | 0.15 weight-% | e.g. 880131 | Robertet Group |
| Water | 6.15 weight-% | | |

Other specific examples of suitable compositions are:

| Ingredient | Amount | Brand | Manufacturer |
|---|---|---|---|
| 1. | | | |
| Starch syrup (40 DE) | 68.35 weight-% (DS) | Reppos 40 | Lantmannen Reppe, Sweden |
| Vegetable fat | 18 weight-% | Akotres M50 | AAK AB |
| Gelatine (type A, 220 bloom) | 2 weight-% | SG-718 | Gelita Sweden AB |
| Malic acid | 1 weight-% | Regular grade, ECC | Bartek Ingredients Inc |
| Lecithin | 0.20 weight-% | Leciprime 1550 | Cargill |
| Colour | 0.30 weight-% | | |
| Flavour | 0.15 weight-% | | |
| Water | 10 weight-% | | |
| 2. | | | |
| Maltose syrup | 48.25 weight-% (DS) | C* Sweet 01656 | Cargill Nordic A/S |
| Sucrose | 20 weight-% | Granulated sugar 500 | Nordic Sugar |
| Vegetable fat | 21 weight-% | Cremoflex L plus | Hobum Oele und Fette GmbH |
| Gelatine (type A, 260 bloom) | 1.30 weight-% | SG 722-Low viscosity | Gelita Sweden AB |
| Citric acid E330 | 1.90 weight-% | Citronsyra 1-Hydrat | Univar AB |
| Sugar ester E473 | 0.50 weight-% | Ryoto Sugar Ester S-570 | Mitsubishi Kagaku Food Corp. |
| Colour, e.g. carmine | 0.30 weight-% | Carrmine 10% | Kanegrade Limited |
| Flavour, e.g. passion fruit | 0.25 weight-% | Safari 6% V | Robertet Group |
| Water | 6.50 weight-% | | |
| 3. | | | |
| Maltitol syrup | 67 weight-% (DS) | Maltidex M 16313 | Cargill Nordic A/S |
| Xylitol | 3 weight-% | Xylitol Crystal 8-40 mesh | Zhejiang Huakang Pharmaceutical Co., Ltd |
| Vegetable fat | 21 weight-% | Cremoflex L plus | Hobum Oele und Fette GmbH |
| Gelatine (type A, 260 bloom) | 1 weight-% | SG 722-Low viscosity | Gelita Sweden AB |
| Malic acid | 1 weight-% | Citronsyra 1-Hydrat | Univar AB |
| Lecithin | 0.20 weight-% | Leciprime 1550 | Cargill |
| Colour, e.g. curcumin 10% | 0.30 weight-% | e.g. K12205 | Kanegrade Limited |
| Flavour, e.g. citrus extract | 0.2 weight-% | e.g. 880131 | Robertet Group |
| Water | 6.30 weight-% | | |
| 4. | | | |
| Maltitol syrup | 70.6 weight-% (DS) | Maltidex M 16313 | Cargill Nordic A/S |
| Vegetable fat | 20.8 weight-% | Cremoflex L plus | Hobum Oele und Fette GmbH |

-continued

| Ingredient | Amount | Brand | Manufacturer |
|---|---|---|---|
| Gelatine (type B, 220 bloom) | 1.1 weight-% | Bovine Hide, PLK142R | Gelita Sweden AB |
| Potassium hydroxide | 0.05 weight % | Caustic Potash, Flakes | Essential Depot, FL, USA |
| Sugar ester | 0.50 weight-% | Ryoto Sugar Ester S-570 | Mitsubishi Kagaku Food Corp. |
| Colour | 0.30 weight-% | | |
| Flavour | 0.15 weight-% | | |
| Water | 6.50 weight-% | | |

5.

| Ingredient | Amount | Brand | Manufacturer |
|---|---|---|---|
| Maltitol syrup | 70.2 weight-% (DS) | Maltidex M 16313 | Cargill Nordic A/S |
| Vegetable fat | 18 weight-% | Akofect SE-U | AAK AB |
| Gelatine (type A, 260 bloom) | 2 weight-% | SG 722-Low viscosity | Gelita Sweden AB |
| Malic acid | 1.90 weight-% | Citronsyra 1-Hydrat | Univar AB |
| Mono-diglycerids | 0.65 weight-% | Cremodan 60 VEG | Danisco |
| Lecithin | 0.05 weight-% | Leciprime 1550 | Cargill |
| Colour | 0.30 weight-% | | |
| Flavour | 0.20 weight-%p | | |
| Water | 6.70 weight-% | | |

The mix of carbohydrates can be selected from the group consisting of mono saccharides, oligosaccharides, polysaccharides, hydrogenated monosaccharides, hydrogenated oligosaccarides or hydrogenated polysaccharides or any combination thereof. Specific examples of carbohydrates that can be present in the mix of carbohydrates are: sucrose, glucose, galactose, lactose, fructose, maltose, maltotrios, trehalose, glycogen, maltodextrin, fructooligosaccharide, dextrin, starch, sorbitol, mannitol, xylitol, maltitol, isomalt, arabitol, erythritol, glycerol, HSH, lactitol, maltotriitol and hydrogenated dextrin.

Examples of ready-made mixtures of carbohydrates of different sorts and lengths that are suitable to use to minimize risk for crystallisation are starch syrup (e.g. corn syrup), maltose syrup, sorbitol syrup, maltitol syrup, isomalt syrup and polyglycitol syrup. When substituting a carbohydrate for another it is important to do this on a dry substance (DS) basis. Different syrups contain different percentage of water and thereby have different dry substance values. Therefore the amount of syrup that should be added has to be adjusted for this. The water content in the final composition must sometimes be adjusted to obtain the same viscosity with the new carbohydrate. The reason for this is that for example longer polysaccharide chains increase the viscosity much more than short mono- or disaccharides and different syrups contains different amounts of short and long polysaccharides (or hydrogenated polysaccharides).

Most types of fat can be used, both liquid (oil) and solid fats. Fats that have been tested successfully include standard rape seed oil, palm kernel oil, sunflower oil and mixes of fats such as Akotres M50, Akofect SE-U, Akomax R and Akofect L from AAK AB and Cremoflex L plus from Hobum Ode and Fette. The choice of fat however imparts the coating mass. For example a fat with a high melting temperature makes the coating dissolve more slowly from the tablet when held in the mouth. If the fat has a melting temperature that is higher than the body temperature, i.e. 37 degrees Celcius, the fat also makes the coating feel rough and gives a higher friction between the coating and the internal part of the mouth. Since it is important that the coated tablet is slippery in order to aid swallowing the present inventors have preferred to have a fat with a melting temperature of 34 degrees Celsius. The percentage of fat has been varied between 5-40 weight-%. Without whishing to be bound by any theories it can generally be said that a higher amount makes the mass softer and the water content therefore has to be decreased to maintain the same viscosity. A higher amount of fat also decreases the stickiness but if the fat content exceeds 40 weight-% (in some cases 30 weight-%, depending on the other ingredients) it can start to affect the stability of the mass resulting in that the gel structure falls apart and the elasticity diminishes and the mass gets greasy. A high amount of fat can also make the coating taste a bit fatty and soapy. Based upon these findings the fat content should be between 5-40 weight-%, preferably between 10-30 weight-% and more preferable between 17-23 weight-%.

The gelatine gives the elasticity to the coating and it can be of different sources and of different types, but the recipe should as said before be adjusted so that the mass pH deviates from the isolectric point of the gelatine in order to obtain a good stability. However, a very low or a high pH of the composition can affect the processability and the taste etc. E.g. a low pH results in that the gelatine breaks down more during manufacture (during boiling) and a high pH can lead to a foul taste. The inventors have therefore in the example of a most suitable composition shown above chosen to use 1.90 weight-% citric acid, which results in a pH of about 2.5. The amount of gelatine must also be adjusted depending on the bloom no of the gelatine so that the same gel strength is obtained. Gelatine with a high bloom value is gelatine with high gel strength and gelatine with a low bloom value is gelatine with low gel strength, i.e. when in gel form with water.

The inventors have preferred to have type A gelatine with an isoelectric point of 8-9 since this makes it easier to deviate from the isoelectric point if having a low pH composition, which is preferred by the inventors in order to get a saliva stimulating coating. A gelatine with a high bloom value of 260 (AOAC) and low viscosity of 3.3 m Pa·s (6.67%, 60 degrees C.) has been preferred since little is needed to obtain a high elasticity and since a low viscosity gelatine makes it easier to fill the heated mass into the device during manufacture. From 0.1 weight-% to 20 weight-% gelatine can be used depending on bloom no, water content and the hardness of the elastic membrane 12, 16 and the size of the membrane opening 13, 17 in the plastic device for applying the coating on a tablet. All other things being equal, a low percentage of gelatine will give a coating that is thinner especially on the edges of tablets while a high percentage makes the coating very thick all over the tablet and it also makes it hard to press a tablet through the device.

An important advantage of the most suitable composition above and the other examples of compositions is that the mass gets a much lower viscosity when heated. This makes it possible to easily deposit the mass into the device in manufacturing. This occurs mainly because the gelatine loses its gel structure and starts to melt above 30-35 degrees Celsius. The gel structure of gelatine is thermo reversible so once the mass cools again to room temperature the gelatine forms a gel structure again. For many other thickening- and gelling agents such as guar gum, xanthan, etc heating have little effect on viscosity, when dissolved in water. Also the maltitol syrup and the fat in the composition get a lower viscosity when heated and do therefore also contribute to this important advantage. The fact that gelatine starts to melt at below normal human body temperature is also advantageous since it decreases the disintegration time of a coating on a tablet that has been swallowed and thereby decreasing the absorption time of any medical substances present in the tablet.

The gelatine content in the coating composition is recommended to be between 0.1-20 weight-%, preferably it should be between 0.3-13 weight-% and more preferably it should be between 0.5-5 weight-%. In the most suitable composition above the gelatine content is 1.32 weight-%. The inventors have not found any suitable substitute to gelatine.

The pH adjusting agent can be of many sorts. Suitable substances that can be used to lower the pH can for example be selected from the group consisting of citric acid, malic acid, lactic acid, ascorbic acid, tartaric acid, fumaric acid, acetic acid, hydrochloric acid, sulphuric acid, gluconic acid, lactic acid, erythorbic acid, phosphoric acid, adipic acid, succinic acid, sorbic acid, formic acid or any combination thereof. Preferably an agent that lowers the pH should be citric acid or malic acid or a mixture thereof and more preferably it should be citric acid.

Suitable substances that can be used to obtain a high pH can for example be selected from the group consisting of sodium carbonate, potassium carbonate, sodium hydroxide, potassium hydroxide, calcium hydroxide, ammonium hydroxide, magnesium hydroxide, calcium oxide, magnesium oxide, trisodium phosphate, trisodium citrate, tripotassium phosphate. Preferably an agent that increase the pH should be trisodium citrate or sodium hydroxide or mixture thereof and more preferably it should be sodium hydroxide.

Substances that lowers the pH and substances that increases the pH of the composition can be used in combination to get a pH modifier (buffer) that assures that the pH of the composition is fixed at a certain level. The amount of the pH adjusting agent could be present in an amount of 0.01-10 weight-%, preferably the amount should be 0.02-7 weight-% and more preferably it should be between 0.02-5 weight-%. However the amount could be higher or lower depending on the strength of the pH modifier.

The emulsifier can be of many different types. The emulsifier can e.g. be chosen from the group of food emulsifiers approved by the European Food Safety Authority consisting of E322, E432, E433, E434, E 435, E436, E442, E470a, E470b, E471, E472a, E472b, E472c, E472e, E472f, E473, E474, E475, E476, E 477, E479b, E481, E482, E491, E492, E493, E494 and E495 or any combination thereof. Preferably the emulsifier should be selected from the group consisting of E322, E471 and E473 or any mix thereof and more preferably the emulsifier should be E473. If adding an emulsifier the emulsifier is recommended to be present in an amount of between 0.01-10 weight-%, preferably between 0.2-3 weight-% and more preferably between 0.2-2 weight-%.

The amount of water to be used in the coating mass varies from 1-35 weight-% depending on type and amount of the other ingredients. All other things equal, increasing the amount of gelatine or carbohydrate makes the composition harder and therefore makes it necessary to increase the water content to maintain the same viscosity. All other things equal, increasing the amount of fat makes the mass softer and makes it necessary to lower the amount of water in the coating composition in order to maintain the same viscosity.

The water content as well as the carbohydrate content and the gelatine content should be adjusted according to the design of the coating device, e.g. the hardness and elasticity of the membrane 16, the size of the membrane 16 and its opening 17 etc.

Colouring has also been added to make the coating look more palatable. The colour has been chosen to reflect the taste. It can be concluded that some colours can lower the gel strength of the coating, for example the food approved emulsifiers E102 and E131. Two examples of colours that so far have been tested successfully are the food approved emulsifiers E100 and E120.

Regarding flavouring some ingredients such as salmiac (ammonium chloride) can lower the gel strength. Examples of flavours which have not been shown to significantly affect the elasticity are natural lemon oil, natural lime oil, natural lemon extract, natural lime extract, all from Robertet SA.

Important advantages of the most suitable composition above as well as the other examples of formulations presented above are that; all of the ingredients are approved as food ingredients and are therefore suitable for ingestion; the coating composition becomes slippery in the mouth and therefore aids in the swallowing of the tablet; the coating compounds dissolve quickly from the tablet in the stomach so that the coating does not encapsulate the tablet and thereby delays the absorption of any active pharmaceutical ingredients present in the tablet; and that the ingredients in the formulations in the present amounts are not commonly known to cause any negative interaction with medical substances.

The most suitable composition has a water activity of less than 0.4 which assures that there cannot be any bacteria-, mould- or yeast growth in the composition. However, other formulations might benefit from addition of food approved preservatives such as benzoic acid or potassium sorbate. Formulations could also benefit from an addition of antioxidants such as the food approved substance ascorbic acid (e.g. to maintain color and flavour) and some formulas might also benefit from addition of stabilizers such as agar or pectin, e.g. to maintain homogeneity or to increase the melting point of the coating composition in order to improve the stability in countries with high outdoor temperatures or to extend the disintegration time of the coating so that it does not disintegrate too fast in the mouth, for example.

Stability tests have been performed on samples of the most suitable composition presented above as well as samples of all specifically described formulas above. In these tests the samples have been stored in air tight containers in about room temperature. Non of the above formulas claimed to be stable did show any notable change of consistency, appearance or taste when stored for one year. This confirms that the preferred coating compositions have the advantage of a long shelf life.

The most suitable composition and the specific examples of suitable compositions can be manufactured by using a cooking technique according to the following procedure: All ingredients except for the gelatine are added to a slurry tank wherein the ingredients are mixed and heated to 60 degrees Celsius (note that the amount of syrup are given on a dry substance (DS) basis). An additional 15% of water (apart from the water in the syrup) can be added to the slurry tank (based on total weight of all ingredients) to easier dissolve all dry ingredients. The gelatine is mixed with two times the amount of water and heated to 80 degrees Celsius and stirred until a uniform consistency is reached. Then the dissolved gelatine is added to the other ingredients in the slurry tank. The mix is then pumped from the slurry tank to a heat exchanger that heats the mass to 107 degrees Celsius. The heat exchanger is connected to a vacuum chamber with absolute pressure of 50 kPa wherein the excess water is boiled away from the mass. The mass is then pumped out from the bottom of the vacuum chamber and fed to a depositor that fills up the coating mass into the coating devices.

The rheological properties of the coating compound has been measured with a Stresstech Rheometer (Reologica Instruments, Lund, Sweden) using a plate-plate geometry with a plate diameter of 30 mm and a gap of 3 mm, in an oscillating mode within a spectrum of frequencies (Hz) at 21 degrees Celcius, 50% RH. The results from this test on the most suitable composition presented above is shown in FIG. 7.

To have suitable rheological properties the composition should at 0.1 Hz frequency have an elastic modulus (G') between 10-1000 000 Pa and a viscous modulus (G") of between 10-1000 000 Pa and at 10 Hz the elastic modulus (G') should be between 100-100 000 000 Pa and the viscous modulus (G") should be between 100-100 000 000 Pa. Preferably the composition should at 0.1 Hz frequency have an elastic modulus (G') between 100-100 000 Pa and a viscous modulus (G") of between 100-100 000 Pa and at 10 Hz the elastic modulus (G') should be between 300-10 000 000 Pa and the viscous modulus (G") should be between 300-10 000 000 Pa. More preferable the composition should at 0.1 Hz frequency have an elastic modulus (G') between 150-10 000 Pa and a viscous modulus (G") of between 300-50 000 Pa and at 10 Hz the elastic modulus (G') should be between 1000-1 000 000 Pa and the viscous modulus (G") should be between 1000-1000 000 Pa.

Figure 7:
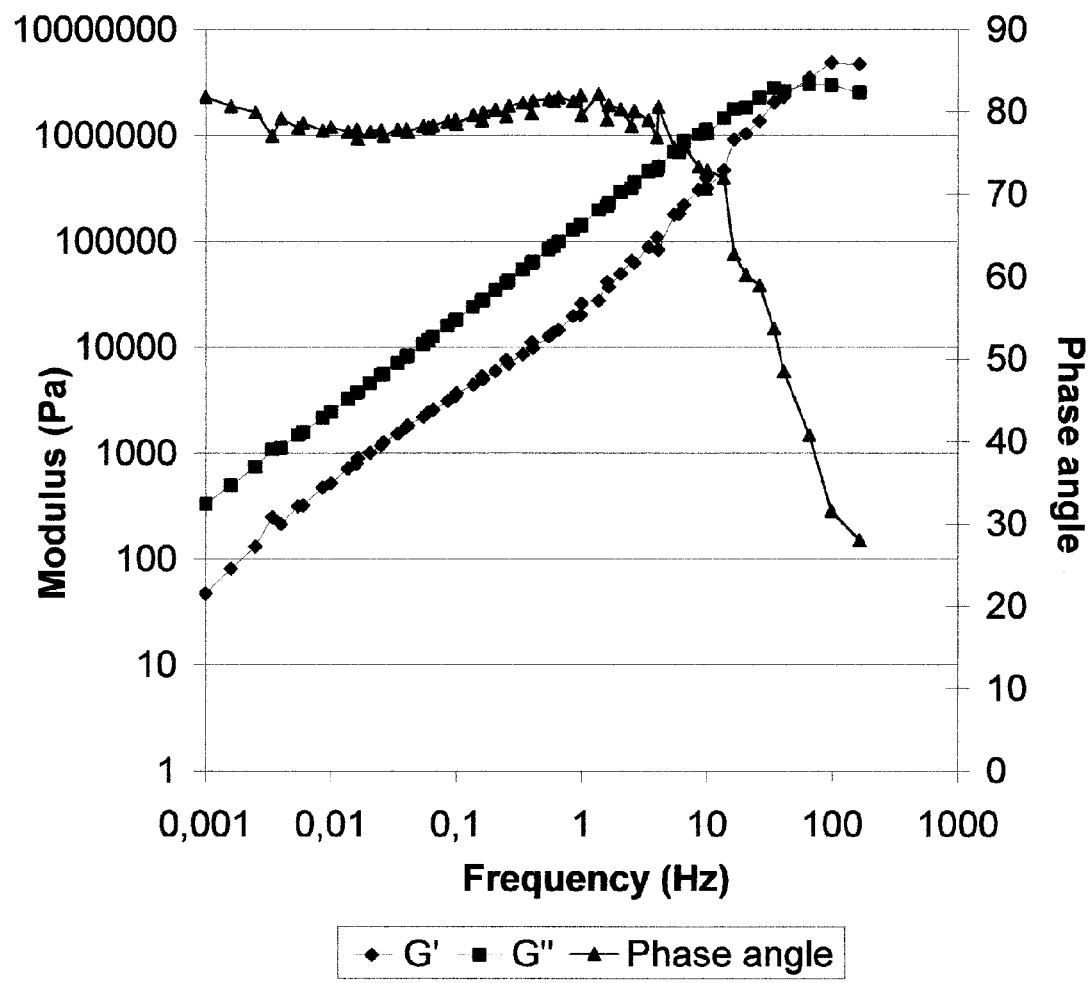
FIG. 7 shows a graph illustrating the rheology of the most suitable coating composition. Viscous- and elastic modulus as well as the phase angle can be seen over a spectrum of frequencies.

As we can see from FIG. 7 the phase angle decreases from 82 degrees at 0.001 Hz frequency down to 28 degrees at 160 Hz frequency. The phase angle shows the viscoelastic properties of the composition. Zero degrees represents an ideal elastic solid while a 90 degrees angle represents an ideal viscous flow liquid. Values in between represents different level of viscoelastic properties, where 45 degrees means that the composition has equal viscous and elastic response (also described as cross over point, where the elastic modulus line and the viscous modulus line crosses each other in the graph). Based on this it is evident that the composition has viscoelastic properties with a cross over at about 50 Hz. Suitable coating compositions should when measured with this test method have a cross over point between 0.01-500 Hz frequency, preferably between 0.1-200 Hz and more preferably between 0.5-100 Hz. The rheological properties of the coating compound has been measured with a Stresstech Rheometer (Reologica Instruments, Lund, Sweden) using a plate-plate geometry with a plate diameter of 30 mm and a gap of 3 mm, in an oscillating mode within a spectrum of frequencies (Hz), at 50% RH and 21 degrees celsius (frequencies above 10 Hz has been obtained with time-temperature super position using also 5 and 13 degrees Celsius). The results from this test on the most suitable composition presented above is shown in FIG. 7.

Figure 8:
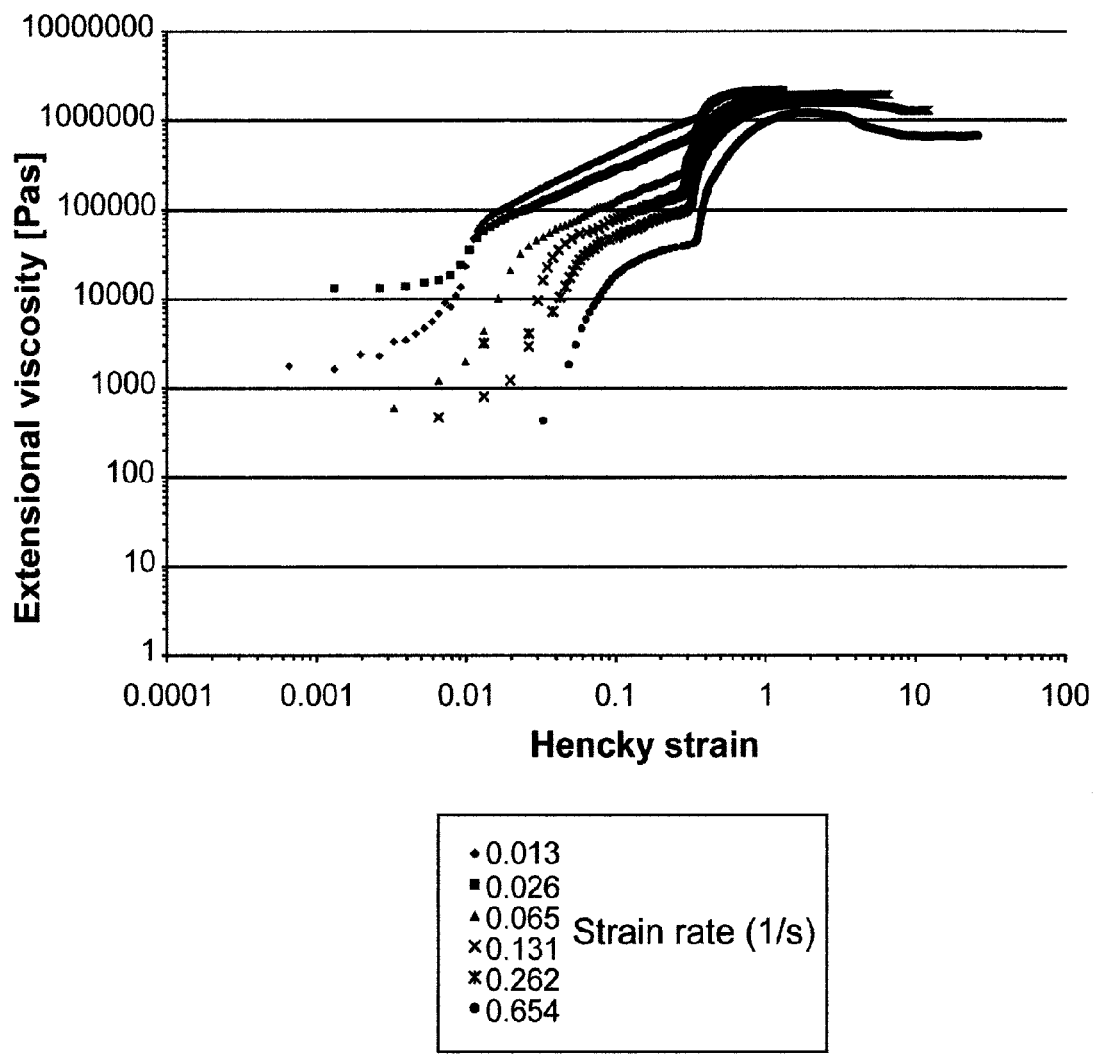
FIG. 8 shows the extensional viscosity of the most suitable coating composition when it is extended.

The rheology has also been measured by measuring the extensional viscosity. Bohlin Reologi AB has developed a test method suitable for semi-solid foods where the sample is subjected to extensional flow in a contraction flow geometry. The test method and equipment is described in the article Wikström, K., Bohlin, L. (1999) "Extensional flow studies of wheat flour dough. 1. Extensional method for measurements in contraction flow geometry and application to flours varying in breadmaking performance", *J Cereal Sci*, 29, 217-226. FIG. 8 shows the extensional viscosity of the most suitable composition above when measured with this test method.

From FIG. 8 it is clear that the coating compound presents a strain hardening rheology during extension. This means that the viscosity and hence the strength of the coating mass increases when it is extended. The coating mass is stressed and extended when pushing a tablet through the device and coatings having strain hardening properties have been shown to form coatings that are more even because of reduced risk for rupture of the coating mass when it becomes thinner due to stress. This since the parts of a coating that has become thinner due to extension can absorb more stress without rupture compared to other areas of the coating that has not been extended as much. It is therefore recommended that the coating mass shows a strain hardening rheology during extension, preferably the coating mass should have a maximum increase in viscosity of at least 1000% during extension and more preferably the mass should have a maximum increase in viscosity of at least 5000% during extension when measured between a henky strain of 0.01-10 with an extension rate of 0.262 rad/s, with the test method and equipment described in the article referred to above.

Figure 9:
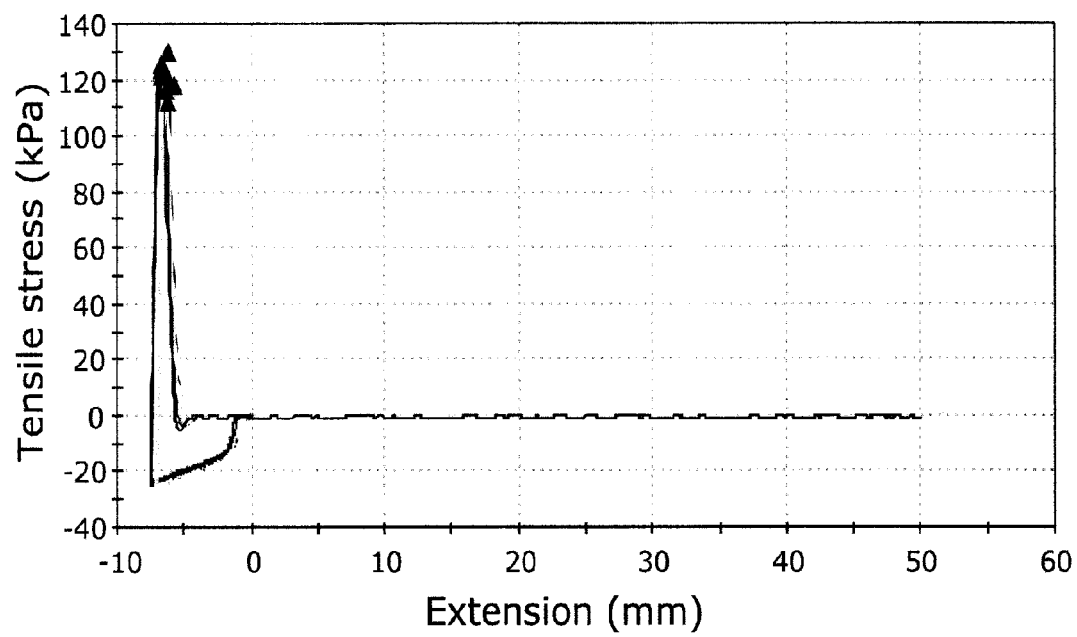
FIG. 9 shows measurements of the stickiness of the most suitable composition presented in the description below.

As describes above it is important that the coating mass has relatively low stickiness to fingers and teeth. The stickiness (adherence) has been measured according to the following procedure:

Measuring instrument: Instron 5542 (Instron Ltd, Canton, Mass., USA). Type of measuring probe: 5 mm diameter cylinder stainless steel. The test was performed at 21 degree Celsius and 50% RH. The sample was compressed at a constant rate of 0.5 mm/s until a force of 0.5 N was reached. The sample was allowed to relax for 10 seconds, and the maximum load (N) when said probe was pulled up at a rate of 16 mm/s was taken to represent stickiness. When measuring with this test method the most suitable composition presented above had a relatively low stickiness. In FIG. 9 the data for this measurement on the most suitable composition is presented. The mean maximum tensile stress was 123.66 kPa which corresponds to 0.12 Newton per square millimeter. Since the probe area is 19.63 mm the total mean load is 2.43 N.

When using the device described above and in FIG. 6a-c (in 21 degrees Celsius), filled with the most suitable composition described above to coat an uncoated tablet with the dimensions 15.1×7.8×5.7 mm the dimensions increase to approximately 17.0×8.7×6.5 mm and the weight increases from 0.55 gram to approximately 0.80 gram. When put in 37 degrees Celsius water that is stirred with 60 rounds per minute the coating dissolves from the tablet within about 1 minute. In reality, for an ingested coated tablet the coating can dissolve much faster since the stomach contains enzymes and hydrochloric acid that can speed up the dissolution. The coating is also partially mechanically rubbed from the tablet during swallowing, which further reduces the dissolution time.

The invention can also be utilized as a toy candy product wherein e.g. sugar pills or the like are coated with coatings with different flavours and colours.

The product can apart for humans, also be used in order to make tablets, capsules and pills more palatable and easy to swallow for animals. When formulating a product for animals the coating composition sometimes has to be modified with regard to flavouring and melting point of the ingredients used, for example.

Although the present invention has been described in considerable detail with reference to certain embodiments, one skilled in the art will appreciate that the present invention can be practiced by other than the described embodiments and examples, which have been presented for purposes of illustration and not of limitation. Therefore, the scope of the appended claims should not be limited to the description of the examples contained herein.

The invention claimed is:

1. A method for coating a solid oral dosage form with a coating composition, said method comprising:
   providing a device comprising a bowl formation holding said coating composition, said bowl formation comprising an elastic diaphragm at a bottom of said bowl formation and having a penetrable opening permitting passage of said solid dosage form and
   pushing said solid dosage form through said penetrable opening to apply said coating composition to said solid dosage form
   wherein:
   said bowl formation contains a coating composition comprising 50%-93.5 weight-% of a mixture of at least two carbohydrates selected from the group consisting of a monosaccharide, an oligosaccharide, a polysaccharide, a hydrogenated monosaccharide, a hydrogenated oligosaccharide, a hydrogenated polysaccharide, and combinations thereof; 0.1-20 weight-% gelatine; 1-35 weight-% water; and a pH adjusting agent and
   said coating composition has a pH that differs from an isoelectric point of said gelatine by at least 2 pH units.

2. The method of claim 1, wherein the pH adjusting agent is present in the coating composition in an amount of 0.01-10 weight-%.

3. The method of claim 1, wherein said gelatine is type A gelatin and said pH adjusting agent is an acid or wherein said gelatine is type B gelatin and said pH adjusting agent is a base.

4. The method of claim 1, wherein said mixture of at least two carbohydrates comprises a syrup.

5. The method of claim 1, wherein said mixture of at least two carbohydrates is selected from the group consisting of starch syrup, maltose syrup, sorbitol syrup, maltitol syrup, isomalt syrup, polyglycitol syrup, and combinations thereof.

6. The method of claim 1, wherein said mixture of at least two carbohydrates comprises two or more carbohydrates selected from the group consisting of sucrose, glucose, galactose, lactose, fructose, maltose, maltotrios, trehalose, glycogen, altodextrin, fructooligosaccharide, dextrin, starch, sorbitol, mannitol, xylitol, maltitol, isomalt, arabitol, erythritol, glycerol, hydrogenated starch hydrosylate (HSH), lactitol, maltotriitol and hydrogenated dextrin.

7. The method of claim 1, wherein the coating composition further comprises 5-40 weight-% of a fat and 0.01-10 weight-% of an emulsifier.

8. The method of claim 1, wherein the coating composition comprises 55-90 weight-% of said mixture of at least two carbohydrates; 0.3-9 weight-% gelatine; 1-20 weight-% water; 7-35 weight-% fat; 0.025-8 weight-% emulsifier; and 0.01-10 weight-% pH adjusting agent.

9. The method of claim 1, wherein the coating composition comprises 60-85.8 weight-% sugar alcohols; 0.5-5 weight-% gelatine; 1-20 weight-% water; 10-30 weight-% fat; 0.05-5 weight-% emulsifier; and 0.01-10 weight-% pH adjusting agent.

10. The method of claim 1, wherein an elastic modulus (G') and a viscous modulus (G") of said coating composition at 0.1 Hz frequency is between 10 and $10^6$ Pa and an elastic modulus (G') and a viscous modulus (G") of said coating composition at 10 Hz frequency is between 100 and $10^8$ Pa.

11. The method of claim 1, wherein said coating composition exhibits a strain hardening rheology during extension.

12. A viscoelastic coating composition for application to a tablet, a capsule, or a pill, said viscoelastic coating composition comprising:
   50%-93.5 weight-% of a mixture at least two carbohydrates selected from the group consisting of a monosaccharide, an oligosaccharide, a polysaccharide, a hydrogenated monosaccharide, a hydrogenated oligosaccharide, a hydrogenated polysaccharide, and combinations thereof;
   0.1-20 weight-% gelatine;
   1-35 weight-% water; and
   0.01-10 weight-% of a pH adjusting agent
   wherein said coating composition has a first elastic modulus (G') and a first viscous modulus (G") at 0.1 Hz in a range of between 10 and $10^6$ Pa and a second elastic modulus (G') and a second viscous modulus (G") at 10 Hz frequency in a range of between 100 and $10^8$ Pa; and
   said coating composition has a pH that differs from an isoelectric point of said gelatine by at least 2 pH units.

13. The viscoelastic coating composition of claim 12, wherein said gelatin is type A gelatin having an isoelectric point of from 8 to 9.

14. The viscoelastic coating composition of claim 12, wherein said mixture of at least two carbohydrates is selected from the group consisting of starch syrup, corn syrup, maltose syrup, sorbitol syrup, maltitol syrup, isomalt syrup, polyglycitol syrup, and mixtures thereof.

15. The viscoelastic coating composition of claim 12, wherein said mixture of at least two carbohydrates comprises two or more carbohydrates selected from the group consisting of sucrose, glucose, galactose, lactose, fructose, maltose, maltotrios, trehalose, glycogen, altodextrin, fructooligosaccharide, dextrin, starch, sorbitol, mannitol, xylitol, maltitol, isomalt, arabitol, erythritol, glycerol, hydrogenated starch hydrosylate (HSH), lactitol, maltotriitol and hydrogenated dextrin.

16. A system for coating a tablet, a capsule, or a pill, said system comprising:
   a device comprising a bowl formation comprising a diaphragm at a bottom of said bowl formation, said diaphragm comprising a conveniently penetrable opening or weakened zone permitting passage of the tablet, capsule, or pill though said opening or weakened zone; and
   the viscoelastic coating composition according to claim 12.

17. The system of claim 16, wherein said device comprises a plurality of bowl formations containing a coating composition comprising 50%-93.5 weight-% of a mixture at least two carbohydrates selected from the group consisting of a monosaccharide, an oligosaccharide, a polysaccharide, a hydrogenated monosaccharide, a hydrogenated oligosaccharide, a hydrogenated polysaccharide, and combinations thereof; 0.1-20 weight-% gelatine; and 1-35 weight-% water.

18. The system of claim 16, wherein a top of said bowl formation is covered by a detachable or penetrable foil.

* * * * *